United States Patent [19]

Dombek

[11] Patent Number: 4,897,473

[45] Date of Patent: Jan. 30, 1990

[54] HOMOLOGATION OF CARBONYLOXY CONTAINING COMPOUNDS

[75] Inventor: Bernard D. Dombek, Charleston, W. Va.

[73] Assignee: Union Carbide Chemicals and Plastics Company Inc., Danbury, Conn.

[21] Appl. No.: 259,378

[22] Filed: May 1, 1981

Related U.S. Application Data

[63] Continuation-in-part of Ser. No. 145,021, Apr. 30, 1980, abandoned, which is a continuation-in-part of Ser. No. 971,666, Dec. 21, 1978, abandoned.

[51] Int. Cl.$^4$ .................. C07C 51/10; C07C 51/353; C07C 67/333; C07C 67/36; C08B 11/12; C08B 13/00
[52] U.S. Cl. .................................. 536/97; 260/397.1; 260/410.9 R; 260/413; 549/292; 556/145; 560/1; 560/80; 560/81; 560/100; 560/105; 560/118; 560/127; 560/169; 560/179; 560/190; 560/205; 560/232; 560/265; 562/400; 562/408; 562/476; 562/478; 562/480; 562/488; 562/489; 562/490; 562/493; 562/496; 562/500; 562/509; 562/511; 562/517; 562/565; 562/579; 562/595; 562/598; 562/606; 536/66

[58] Field of Search ............... 562/598, 517, 606, 480, 562/488, 489, 595, 500, 400, 509, 408, 490, 493, 496, 511, 476, 478; 560/265, 190, 205, 232, 105, 100, 127, 1, 80, 81, 118, 169, 179; 536/97, 124, 66

[56] References Cited

U.S. PATENT DOCUMENTS

| | | | |
|---|---|---|---|
| 3,816,490 | 6/1974 | Forester et al. | 260/413 |
| 4,124,647 | 11/1978 | McVicker | 568/671 |
| 4,132,734 | 1/1979 | Singleton | 562/522 |
| 4,169,853 | 10/1979 | Knifton | 564/417 |
| 4,189,441 | 2/1980 | Braca | 562/517 |
| 4,226,845 | 10/1980 | Laine | 568/882 X |
| 4,260,820 | 4/1981 | Knifton | 562/517 |
| 4,319,038 | 3/1982 | Kubbeler et al. | 560/232 |

FOREIGN PATENT DOCUMENTS

857270 1/1978 Belgium .

OTHER PUBLICATIONS

G. Braca et al., Journal of American Chemical Society, 100:19, Sep. 13, 1978.

*Primary Examiner*—Vivian Garner
*Attorney, Agent, or Firm*—Reynold J. Finnegan

[57] ABSTRACT

This invention produces higher homologs, i.e., differing by at least a —$CH_2$-unit, of carbonyloxy-containing compounds by treating the carbonyloxy-containing compounds with carbon monoxide and hydrogen in the presence of a ruthenium-containing compound, a proton donor, an iodide promoter, and optionally, a manganese-containing compound.

10 Claims, No Drawings

HOMOLOGATION OF CARBONYLOXY CONTAINING COMPOUNDS

GENERAL DESCRIPTION OF THE INVENTION

This invention is directed to the formation of higher homologs, i.e., differing by at least a —$CH_2$ unit, of carbonyloxy-containing compounds. This process treats carbonyloxy-containing compounds with carbon monoxide and hydrogen in the presence of a ruthenium-containing compound, a proton donor, a halogen promoter, and optionally, a manganese-containing compound whereby such carbonyloxy-containing compound is converted to a higher homolog differing by at least an additional —$CH_2$-unit in the position alpha to the carbonyl of the carbonyloxy group.

DISCUSSION OF THE PRIOR ART

D. J. Cram and G. S. Hammond in "Organic Chemistry", McGraw-Hill, 2nd Ed., 1964, p. 18, describe a homologous series as a series of compounds in which each member differs from the next member by a constant amount, the members being homologs of one another.

On page 496 of this text is described the Arndt-Eistert synthesis, in which a carboxylic acid is converted to its next-higher homolog (homologated) by a multi-step procedure involving diazomethane.

Belgium Patent No. 857,270, published July 28, 1976, describes the homologation of esters wherein the alcohol portion of the ester is increased by the addition of $CH_2$. According to the Belgium patent, an ether or an ester is reacted with carbon monoxide and hydrogen at a temperature of 150°–350° C. and a pressure of 50–1000 atmospheres in the presence of a catalyst containing a ruthenium carbonyl and as a promoter, HI, or a solution of mineral or tetralkylammonium iodides or bromides, or their mixtures in a carboxylic acid. Illustrative of the kinds of products produced is shown in an example, which shows the carbonylation and homologation of dimethyl ether using tricarbonyl allyl ruthenium chloride and methyl iodide as the catalyst and promoter, respectively. The reaction is effected in an autoclave to which hydrogen and carbon monoxide are added at a temperature of 200° C. and a pressure of 240 atmospheres. The molar ratio of hydrogen to carbon monoxide is 2:1. The products of the reaction are 12.8% methane, 13% alcohols, 4.5% ether, 42.5% methyl acetate (the carbonylation product), 16% ethyl acetate (the carbonylation and homologation product), and 6% acids (indicating the presence of acetic and propionic acid). The origin of the propionic acid is not discussed and it is only a very minor component of the total products.

Belgium Patent No. 857,270 discloses that carboxyl acids may be employed as solvents for the process of Belgium Patent No. 857,270 and that if acetic acid is employed as the solvent in the carbonylation reaction of dimethylether in ethyl acetate that methyl acetate is formed and may be considered as an intermediate product. The use of carboxyl acids as solvents is further exemplified in examples 5 and 10 to 18 of Belgium Patent No. 857,270.

The advance of the technology of this invention is the ability to introduce one or more —$CH_2$-groups adjacent or alpha to the carbonyl of a carbonyloxy group. This process has heretofore never been achieved in one step.

During the present process, the homologation of the carbonyloxy-containing compound is achieved in a single reactor essentially at one period of time. The utility of this process is that it allows the production, in a single step, of higher homologs of carbonyloxy-containing compounds differing from the starting compound by at least one methylene group. Also, the present process may be used to produce compounds which may not be produced conveniently by other synthesis methods.

Therefore, the process of this invention is fundamentally unconcerned with the structure of the carbonyloxy-containing compound since whatever carbonyloxy-containing compound is used, homologation is achieved and the benefits of the invention will be realized. Moreover, should a carboxylic acid, ester, or anhydride become altered in any way in the present process, such will be in addition to the alteration achieved by homologation.

THE INVENTION

This invention relates to the formation of higher homologs, i.e., differing by at least a —$CH_2$-unit, of carbonyloxy-containing compounds. More particularly, this invention is concerned with the treatment of carbonyloxy-containing compounds with carbon monoxide and hydrogen in the presence of a ruthenium-containing compound, a proton donor, an iodide promoter, and optionally, a manganese-containing compound whereby such carbonyloxy-containing compounds are converted to a higher homolog differing by at least an additional —$CH_2$-unit, in some instances differing by (—$CH_2$-)$_n$ units, wherein n has a value of 1 to about 6, or more, in the position alpha to the carbonyl of the carbonyloxy groups of the compounds.

The process is effected by reacting a carbonyloxy-containing compound with a mixture of carbon monoxide and hydrogen in the presence of a ruthenium-containing compound, preferably a ruthenium carbonyl complex, either formed in situ or formed prior to the reaction, in the presence of a proton donor such as an acid, an iodide promoter, and optionally, a manganese-containing compound.

The carbonyloxy-containing compound which can be homologated according to the process of this invention is essentially any carbonyloxy-containing compound, ranging from formic acid to fatty acids, and to essentially any carboxylic acid, and esters and anyhdrides thereof. As long as a compound contains the carbonyloxy radical:

in which the free valence of the oxy(—O—) group is bonded to carbon or hydrogen, it can be used in the process of this invention to form higher homologous compounds.

Preferred carbonyloxy-containing compounds are of the formulae:

(I)

wherein R and R° are monovalent radicals such as hydrogen, hydroxyl, carboxyl and any organic radical bonded to the —C=O, and R' is a monovalent organic radical bonded to the oxide of the carbonyloxy group; R together with R' or R together with R° can form a cyclic compound. These carbonyloxy-containing compounds produce a higher homolog of the formulae:

$$R(CH_2)_m\overset{O}{\underset{\|}{C}}OH \text{ and } R°(CH_2)_n\overset{O}{\underset{\|}{C}}{-}OH \quad (II)$$

wherein n and m have values of at least 1 and typically not in excess of about 6 and R and R° are as previously defined.

Illustrative of such carbonyloxy containing compounds are the following polycarboxylic acids, esters, or anhydrides of the formula:

$$(R'')_a(-\overset{O}{\underset{\|}{C}}{-}OR''')_b$$

wherein R" is any polyvalent organic radical or a bond joining two —COOR''' groups; R''' is H or a monovalent organic radical; a is 0 or 1; b is equal to the free valence of R" or 2 when a is 0. The size and composition of R" or R''' are not important to the process of this invention, since they do not affect the operativeness of the process.

Further illustrative carbonyloxy-containing compounds include the following: carbonic acid, the esters of carbonic acid, whether monomers or polymers (viz., polycarbonates), formic acid and its esters regardless of the size and composition of the ester moiety, fatty acids of $C_1$ to greater than $C_{20}$ in size, regardless of whether they are normal, secondary or tertiary carboxylic acids, aromatic monocarboxylic acid esters and their anhydrides, ethylenically unsaturated carboxylic acids such as tiglic acid, ricinoleic acid and their esters regardless of the size and composition of the ester moiety, cycloaliphatic monocarboxylic acids such as cyclohexanecarboxylic acid, 2-norbornyl carboxylic acid, 2-norborn-5-enyl carboxylic acid and their esters regardless of the size and composition of the ester moiety, aromatic monocarboxylic acid, such as benzoic, benzylic, toluic, naphthaoic acids and their esters regardless of the size and composition of the ester moiety, substituted alkanoic acids, such as the protein acids, glycolic acids, hydroxyl carboxylic acids, phenyl-substituted fatty acids (larger than benzylic, illustrated above), carboxymethyl-cellulose, ascorbic acids, tannic acid, steroid acids such as cholanic acid, ferrocenyl carboxylic acid, and the like, and their esters regardless of the size and composition of the ester moiety, aliphatic dicarboxylic acids starting from oxalic acid, malonic acid through maleic acid, fumaric acid, adipic acid to 1,12-dicarboxydodecane and their esters regardless of the size and composition of the ester moiety, aromatic dicarboxylic acids such as phthalic acid, isophthalic acid, terephthalic acid, naphthyl dioic acids, anthracyl dioic acids, polyphenylene dioic acids, and their esters regardless of the size and composition of the ester moiety, cycloaliphatic dicarboxylic acids such as 1, 4-cyclohexane dicarboxylic acid, 1, 3-cyclohexane dicarboxylic acid, and their esters regardless of the size and composition of the ester moiety, tricarboxylic acids such as trimellitic and pyromellitic acid and their esters regardless of the size and composition of the ester moiety, tetracarboxylic acids, such as ethylene diamine-N,N',N'',N'''-tetraacetic acid, telomers of acrylic acid, and their esters, regardless of the size and composition of the ester moiety, polymeric carboxylic acids, such as the homopolymers of acrylic acid, and methacrylic acid.

If the carbonyloxy-containing compound possesses groups which for one reason or another will inhibit or inactivate the catalyst, a simple technique for overcoming the inhibition of the reaction is to provide an additional amount of catalyst to exceed the capacity of the inhibiting component from preventing homologation.

The ruthenium-containing compounds which effect the homologation reaction herein may be one or more of the following compounds:

$RuO_2$
$Ru(CO)_5$
$Ru_3(CO)_{12}$
$H_2Ru_4(CO)_{13}$
$H_4Ru_4(CO)_{12}$
$Ru(CO)_3L_2$
$Ru(CO)_4L$
$Ru_3(CO)_{11}L$
$Ru_3(CO)_{10}L_2$
$Ru_3(CO)_9L_3$
$RuX_2L_4$, X=Cl, Br, I
$RuX_2L_3$, X=Cl, Br, I
$RuX_2(CO)_2L_2$, X=Cl, Br, I
$RuX_3L_2(CH_3OH)$, X=Cl, Br, I
$[C_6H_5NH][RuX_4(CO)(C_6H_5N)]$, X=Cl, Br, I
$[Ru(CO)_3X_2]_2$, X=Cl, Br, I
$Ru(CO)_2X_2[(C_6H_5)_2P\,CH_2CH_2P(C_6H_5)_2]$, X=Cl, Br, I
$RuXHL_3$, X=Cl, Br, I
$RuH_2L_4$
$RuH_4L_3$
$RuH_2(N_2)\,L_3$
$RuH_2(CO)\,(L)_3$
$RuX_3(NO)L_2$, X=Cl, Br, I
$Ru(NO)_2L_2$
$RuH_2(CH_3CN)L_3$
$Ru(OAc)H(L)_3$
$[RuX_3(NO)]_n$, X=Cl, Br, I
$[As(C_6H_5)_4][RuX_4(CO)]$, X=Cl, Br, I
$[LH][RuX_4L_2]$ X=Cl, Br, I
$Ru_2X_3(SnX_3)\,(CO)_2L_4$, X=Cl, Br, I
$(n^6\text{-}C_6H_6)\,Ru\,(CH_3)\,XL$, X=Cl, Br, I
$[(n^6\text{-}C_6H_6)(n^5\text{-}C_5H_5)Ru]X$, X=Cl, Br, I
$[(n^6\text{-}C_6H_6)RuX_2]_2$, X=Cl, Br, I Suitable classes of triorgano-containing ligands (L in the formulas, supra) which are contemplated in the practice of the invention include the trialkylphosphites, the tricycloalkylphosphites, the triarylphosphites, the triarylphosphines, the triarylstibines, and the triarylarsines. Desirably, each organo moiety in the ligand does not exceed 18 carbon atoms. The triarylphosphites and the triarylphosphines represent the preferred classes of ligands. Specific examples of ligands which re suitable for use herein include:

$P(CH_3)_3$
$P(C_2H_5)_3$
$P(n\text{-}C_3H_7)_3$
$P(n\text{-}C_4H_9)_3$
$P(iso\text{-}C_4H_9)_3$
$P(n\text{-}C_5H_9)_3$
$P(2\text{-}n\text{-}C_4H_9OC_2H_4)_3$
$P(2\text{-}C_6H_5C_2H_4)_3$
$P(C_6H_{11})_3$ P(CH$_3$)(C$_2$H$_5$)$_2$
P(CH$_3$)$_2$(C$_2$H$_5$)
P(CH$_3$)$_2$(C$_6$H$_5$)
P(C$_2$H$_5$)$_2$(C$_6$H$_5$)
P(C$_6$H$_{11}$)$_2$(2-CNC$_2$H$_4$)
P(CH$_3$)$_2$(2-CNC$_2$H$_4$)
P(n-C$_4$H$_9$)$_2$(2-CNC$_2$H$_4$)
P(n-C$_3$H$_{17}$)$_2$(2-CNC$_2$H$_4$)
P(p-CH$_3$OC$_6$H$_4$)$_3$
P(C$_6$H$_5$)$_3$
P(C$_6$H$_5$)$_2$(C$_2$H$_5$)
P(C$_6$H$_5$)$_2$(n-C$_4$H$_9$)
P(O-n-C$_4$H$_9$)$_3$
P(OCH$_3$)$_3$
P(OC$_6$H$_5$)$_3$ The aforementioned ruthenium compounds should not be considered to be the defined catalyst effecting the homologation reaction. These ruthenium compounds are precursors and during the operation of the process it is believed that the catalytic species which helps promote the homologation reaction is formed. Thus, a considerable number of different ruthenium compounds may be employed herein. Particularly useful are the ruthenium compounds which contain iodine as aforedescribed, since the iodine can be utilized as part of the promoter enhancing the homologation reaction.

One or more halogen components may be complexed with the ruthenium as ligands thereon. However, it is preferred to have an excess of the halogen, iodine, present in the catalyst system as a promoting component. By excess of iodine is meant an amount greater than 2 atoms of iodine per atom of ruthenium. This promoting component of the catalyst system may be iodine and/or an iodine compound such as hydrogen iodide, alkyl or aryl iodide, metal iodide, ammonium iodide, phosphonium iodide, arsonium iodide, stibonium iodide and the like. Exemplary suitable iodine providing or promoting components may be selected from the following iodine and/or iodine-containing compounds:

R$_1$I wherein R$_1$ is any alkyl or aryl group e.g., CH$_3$I, C$_6$H$_5$I, CH$_3$CH$_2$I, etc.;

I$_2$ or I$_3$— etc.;

HI;

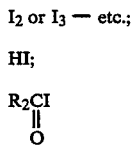

wherein R$_2$ is any alkyl or aryl group, e.g.,

etc.;

R$_4$MI, R$_4$MI$_3$, or R$_3$MI$_2$ wherein R is hydrogen or any alkyl, M is N, P, As, or Sb, e.g., NH$_4$I, PH$_4$I$_3$, PH$_3$I$_2$, (C$_6$H$_3$)$_3$PI$_2$, and/or combination of R and M.

A wide variety of manganese-containing compounds may also be used in the practice of this invention. Illustrative of suitable manganese-containing compounds are the following: manganese carbonyl, manganese halides, manganese carboxylates, manganese enolates, manganese oxides, manganese salts of other inorganic acids, manganese alkyls, arene complexes with manganese, olefin complexes with manganese, and the like. Specific illustrations of suitable manganese-containing compounds which may be used as cocatalysts in the practice of this invention are the following:

Cyclopentadienyl Manganese Tricarbonyl
C$_5$H$_5$Mn(CO)$_3$
Dipyridine Manganese Dichloride
(C$_5$H$_5$N)$_2$MnCl$_2$
Manganese Acetate
Mn(C$_2$H$_3$O$_2$)$_2$
Manganese Acetylacetonate (ic)
Mn(CH$_3$COCHCOCH$_3$)$_3$
Manganese Acetylacetonate (ous)
Mn(CH$_3$COCHCOCH$_3$)$_2$
Manganese (III) Benzoylacetonate
Mn(C$_6$H$_5$COCHCOCH$_3$)$_3$
Manganese Carbonyl
Mn$_2$(CO)$_{10}$
Manganese Formate
Mn(O$_2$CH)$_2$
Manganese (II) Hexafluoroacetylacetonate
(CF$_3$COCHCOCF$_3$)$_2$Mn
Manganese Naphthenate
Mn(Naphthenate)$_2$
Manganese Octoate
Mn[COO(C$_2$H$_5$)CHC$_4$H$_9$]$_2$
Manganese Oxalate
MnC$_2$O$_4$.2H$_2$O
Manganese Pentacarbonyl Bromide
Mn(CO)$_5$Br
Manganese Stearate
Mn(C$_{18}$H$_{36}$O$_2$)$_2$
Manganese (II) Trifluoroacetylacetonate
Mn(CF$_3$COCHCOCH$_3$)$_2$
Methylcyclopentadienyl Manganese Tricarbonyl
CH$_3$C$_5$H$_4$Mn(CO)$_3$
bis-(Tripnenylphosphine)Imminium
Pentacarbonylmanganate (PPh$_3$)$_2$Mn(CO)$_5$
Manganese (II) bromide
MnBr$_2$.4H$_2$O
Manganese (II) carbonate
MnCO$_3$
Manganese (II) chloride,
MnCl$_2$
Manganese (II) chloride,
MnCl$_2$.4H$_2$O
Manganese (II) fluoride
MnF$_2$
Manganese (III) fluoride
MnF$_3$
Manganese (II) iodide
MnI$_2$.4H$_2$O
Manganese (II) nitrate
Mn(NO$_3$)$_2$
Manganese (II, III) oxide
Mn$_3$O$_4$
Manganese (III) oxide
Mn$_2$O$_3$
Manganese (IV) oxide
MnO$_2$
Manganese (II) perchlorate
Mn(ClO$_4$)$_2$.6H$_2$O
Manganese (II) sulfate
MnSO$_4$.H$_2$O Potassium hexacyanomanganate (II)
$K_4Mn(CN)_6 \cdot 4H_2O$
Potassium permanganate
$KMnO_4$ The amount of promoting component employed in the catalyst system of the present invention is such as to provide a ratio of halogen atoms to manganese atoms of from about 2:1 to 50,000:1 and higher. The preferred ratio is 3:1 to 5,000:1, while the more preferred ratio is 5:1 to 2500:1 halogen atoms to manganese atoms.

The quantity of the catalyst which is employed is not narrowly critical and can vary over a wide range. In general, the process of this invention is desirably conducted in the presence of a catalytically effective quantity of the active ruthenium species, or optionally, of the active ruthenium and manganese species which gives a suitable and reasonable reaction rate. The reaction proceeds when one employs as little as about $1 \times 10^6$ weight percent of ruthenium or even a lesser amount (calculated as the metal in the complex catalyst) based on the total quantity of reaction mixture. The upper concentration can be quite high, e.g., about ten weight percent or more of ruthenium based on the total quantity of reaction mixture. Higher concentrations may be used if desired. However, the upper concentration appears to be dictated by economics in terms of the cost of the catalyst to achieve the given reaction and ease of handling of the homogeneous phase reaction mixture during the course of reaction. Depending on various factors, such as the acyl compound of choice, the partial pressures of carbon monoxide and hydrogen, the total operative pressure of the system, the operative temperature, the choice of the solvent, if any, and other considerations a concentration of between about $1 \times 10^{-5}$ to about 10 weight percent of ruthenium or of each of ruthenium and manganese (contained in the complex catalyst) based on the total quantity of the homogenous liquid phase reaction mixture is generally suitable in the practice of this invention.

The proton donor which may be used herein additionally includes hydrogen halides as well as other acids. The amount of proton donor which may be employed herein is such as to provide a molar ratio of proton donor to manganese plus ruthenium atoms of from about 2:1 to 50,000:1 and higher.

The present process is typically effected in the presence of a liquid phase which may be homogeneous or heterogeneous depending upon the solubility of the carbonyloxy compound in the liquid phase. If the carbonyloxy compound is a highly cross-linked structure, then a solvent is selected which is sufficiently polar to allow sufficient wetting of the carbonyloxy moieties of the molecule, which allows the homologation to occur at the interface. Otherwise, there is no strict rule in the selection of a solvent. Essentially any liquid in which the catalyst components are soluble may be utilized as a solvent in the practice of this invention. However, if selection of a solvent includes a material which would adversely affect the catalytic activity of the catalyst, then of course, under those circumstances an excess of catalyst is employed to overcome the poison effect of the solvent or a solvent is selected which is not a poison. The solvent may be inert to the reactions which are taking place in the process or may participate in the reaction in a homogeneous liquid phase reaction mixture to produce the desired product. In some respects, the solvent may be a material which will react with another material in the mixture to form a third material which acts as a solvent. The solvent may also include the products of the reaction. Particularly illustrative of solvents suitable for use in the practice of this invention are the following: saturated and aromatic hydrocarbons, e.g., hexane, octane, dodecane, naphtha, decalin, tetrahydronaphtnalene, kerosene, mineral oil, cyclohexane, cycloheptane, alkylcycloalkane, benzene, toluene, xylene, naphthalene, alkylnaphthalene, and the like; ethers such as tetrahydrofuran, tetrahydropyran, diethylether, 1,2-dimethoxybenzene 1,2-diethoxybenzene, the mono- and dialkylethers of ethylene glycol, propylene glycol, butylene glycol, diethylene glycol, dipropylene glycol, oxyethylene glycol, and the like; alkanols such as methanol, ethanol, propanol, isobutanol, 2-ethylhexanol, and the like; esters such as methyl acetate, ethyl acetate, propyl acetate, butyl acetate, methyl propionate, ethyl butyrate, methyl laurate, and lactones such as butyrolactone, and the like; water; fluorinated hydrocarbons that are inert under the reaction conditions such as perfluoroethane, monofluorobenzene, and the like. Another class of solvents are sulfones such as dimethylsulfone, diethylsulfone, diphenylsulfone, sulfolane, and the like; and halogenated solvents such as 1,2-dichloroethylene, 1,2-dichloroethane, chloroform, 1-chlorobutane, and 4-bromotoluene, and the like. Mixtures of the aforementioned solvents may be employed so long as they are compatible with each other under the conditions of the reaction and will adequately provide the homogeneous liquid phase for carrying out the process of this invention. Of the aforementioned classes of solvents, hydrocarbons, the sulfones, and the fluorinated hydrocarbons are typically inert in the present process, whereas esters, water and alcohols will in one manner or another enter into a reaction during the course of the process. The esters have the capability of entering into ester interchange and homologation reactions; the water into hydrolysis reactions; and the alcohol into alcohol interchange reactions with esters, into esterification with acyl compound or into carbonylation reactions.

In the preferred embodiment of this invention, the solvent is the acid itself since many of the desirable commercial acids that one would seek to homologate are liquid under the conditions of the homologation reaction.

The present reaction is effected at a temperature which can vary over a wide range, from moderate temperatures to elevated temperatures. In general, the process is conducted at a temperature of between about 50° C. and about 400° C.

Operating the process at temperatures lower than 50° C. will not produce the desired products at an optimum rate so that the reaction will have to be operated over an extended period of time in order to obtain the desired product of reaction. When operating the process at temperatures higher than 400° C. there is a tendency for the reaction products and organic materials contained therein to decompose. Also there is a tendency for the catalytic species to decompose which forms insoluble ruthenium compounds. The formation of insoluble ruthenium compounds can be controlled by increasing the reaction pressure which is generally sufficient to keep the ruthenium catalytic species in solution. In most cases, when operating at the lower end of the temperature range, it is desirable to utilize pressures in the higher end of the pressure range. The preferred temperature range is between about 150° C. and 350° C., while the most preferred temperature range is between about 200° C. and 330° C. However, there are occasions when a preferred temperature range may include any of the more desirable ranges as well as the broadest temperature range such that the process may be operated at a temperature between 100° C. and 325° C. and as well as between about 50° C. and 350° C.

The process of the present invention is effected under superatmospheric pressure conditions. Invariably, the pressure is produced by the hydrogen and carbon monoxide provided to the reaction. Pressures of between about 500 psia (36.535 kg/cm$^2$) and about 12,500 psia (878.8 kg/cm$^2$) represent an operative limit for producing the desired products. However, when operating the process at the lower end of the pressure range, the rate of reaction becomes markedly slow and therefore the reaction period must be extended until the desired amount of reaction product is produced. On the other hand, when the process is operated at a pressure near the high end of the range, the rate of production of the desired products will be increased. However, operating the process at pressures in excess of the upper end of the pressure range is not economically justified. In the preferred practice of this invention, it is desirable to operate the process at a pressure of between about 1000 psia (70.31 kg/cm$^2$) and about 10,000 psia (703.07 kg/cm$^2$). In addition to the partial pressure exerted by carbon monoxide and by hydrogen, a partial pressure will also be exerted by inert gases such as argon, if these are employed in the reaction.

The process of this invention is effected for a period of time sufficient to produce the desired products. In general the reaction time can vary from minutes to several hours, i.e., from a few minutes to approximately twenty-four hours, and longer. If the most sluggish reaction conditions are selected, then the reaction time will have to be extended until the desired product is produced. It is readily appreciated that the residence period will be influenced by the reaction temperature, concentration and choice of the ruthenium catalyst, the promoter, the total gas pressure, and the partial pressure exerted by its components, the concentration and choice of solvent, the particular acyl compound and other factors. The synthesis of the desired products by the reaction of hydrogen, carbon monoxide and the acyl compound is suitably conducted under operative conditions which give reasonable reaction rates and/or conversions.

The relative amounts of carbon monoxide and hydrogen which are initially present in the reaction mixture can be varied over a wide range. In general, the mole ratio of carbon monoxide to hydrogen is in the range of between about 20:1 to 1:20, preferably between about 15:1 and about 1:15, and most preferably between about 10:1 and about 1:10. It is to be understood, however, that molar ratios outside the stated broad range may be employed. Substances or reaction mixtures which form carbon monoxide and hydrogen under the reaction conditions may be employed in lieu of the mixtures of carbon monoxide and hydrogen. For example, one may use mixtures containing carbon dioxide and hydrogen, mixtures of carbon dioxide, carbon monoxide and hydrogen as well as mixtures of steam and carbon monoxide. The intended purpose is to provide enough carbon monoxide in combination with hydrogen in the homogeneous liquid phase mixture to produce the desired product. The manner in which the carbon monoxide and hydrogen are provided in the homogeneous liquid phase reaction mixture is not important in the practice of this invention, as long as they are present in a sufficient quantity to effect the production of the desired products.

The process of this invention can be carried out in a batch, semi-continuous or continuous manner. The reaction may be conducted in a single reaction zone or in a plurality of reaction zones, in series or in parallel. The reaction may be conducted intermittently or continuously in an elongated tubular zone or in a series of zones. The material of construction of the equipment should be such so as to be inert during the reaction. The equipment should also be able to withstand the reaction temperatures and pressures. The reaction zone can be fitted with internal and/or external heat exchangers to control undue-temperature fluctuations, or to prevent possible "run-away" reaction temperatures caused by the exothermic nature of the reaction. In a preferred embodiment of the present invention, agitation means to insure complete mixing of the reaction mixture should be employed. Mixing induced by vibration, shaker, stirrer, rotary, oscillation, ultrasonic etc., all are illustrative of the types of agitation means which are contemplated. Such means are available and well known to the art.

The catalyst may be initially introduced into the reaction zone batch wise. Alternatively, the catalyst may be introduced into the reaction zone, continuously or intermittently during the course of the synthesis reaction. Means to introduce the reactants into the reaction zone during the course of the reaction and/or means to adjust the reactants in the reaction zone during the reaction, either intermittently or continuously, can be conveniently utilized in the process to maintain the desired molar ratios of reactants and to maintain the partial pressures exerted by the reactants.

The operative conditions of the present process may be adjusted to optimize the conversion of the desired product and/or the economics of the process. In a continuous process, for example, it is preferred to operate at relatively low conversions, and it is desirable to recirculate unreacted mixtures of carbon monoxide and hydrogen to the reactor with or without make-up carbon monoxide and hydrogen. Recovery of the desired product can be achieved by methods well-known in the art, such as by distillation, fractionation, extraction, and the like.

Typically, in carrying out the process, the product contained in the homogeneous liquid phase reaction mixture would be withdrawn from the reaction zone and distilled to recover the desired product. Thereafter, if desired, a fraction comprising the catalyst components generally contained in the by-products and/or solvent or acyl compound, can be recycled to the reaction zone. All or a portion of such fraction can be removed for recovery or regeneration of the catalyst. Fresh catalyst components can be intermittently added to the reaction stream or can be added directly to the reaction zone, to replenish any catalyst which is lost in the process.

In another aspect of this invention a novel ruthenium containing catalyst is described. This novel catalyst is capable of homologating carbonyloxy-containing compounds with carbon monoxide and hydrogen. The catalyst is defined as ruthenium complexes which will homologate a carbonyloxy-containing compound when existing in a homogeneous liquid phase mixture in the presence of carbon monoxide, hydrogen, proton donor and iodine promoter, when the mixture is maintained at a temperature of between about 50° C. and about 400° C. and a pressure of between about 500 psia (36.535 kg/cm$^2$) and about 12,500 psia (878.8 kg/cm$^2$). The metal compounds supplied to the homogeneous liquid phase reaction mixture are not themselves catalysts unless hydrogen, carbon monoxide, proton donor and iodine promoter are present and the reaction conditions, as previously described, are maintained. Thus, the aforementioned description with respect to the promoter, the homogeneous liquid phase reaction mixture, the temperature and pressure and the characterization of the products of the reaction are all important in and bear a relationship to the nature of the novel catalyst of this invention.

Although this invention has been described with respect to a number of details, it is not intended that this invention should be limited thereby. The examples which follow are intended solely to illustrate the most favorable embodiments of this invention which to date have determined and are not intended in any way to limit the scope and the intent of this invention.

EXAMPLE 1

A 500 ml stainless steel bomb reactor containing a removable glass liner was charged with a mixture of 0.50 g Ru$_3$(CO)$_{12}$, 0.20 g Mn$_2$(CO)$_{10}$, 2 ml of a solution of 57 percent HI and 50 ml of acetic acid. Equimolar amounts of carbon monoxide and hydrogen were then added to the reactor to attain a pressure therein of 3000 psi at 25° C. The reactor was rocked and the contents heated to 230° C. and maintained at this temperature for four hours with continued rocking of the reactor. The reactor was then cooled and vented. The contents of the reactor were removed and analyzed by gas chromatography. This analysis showed that the following products were produced: 0.08 g methyl acetate, 4.5 g ethyl acetate, 6.5 g propionic acid and 0.9 g butyric acid.

EXAMPLE 2

The procedure of Example 1 was exactly repeated except that the reactor was charged with a mixture of 0.50 g Ru$_3$(CO)$_{12}$, 0.50 g MnI$_2$, 0.5 ml of a solution of 57 percent HI and 50 ml of acetic acid and the contents heated at 200° C. for three hours. Analysis by gas chromatography showed that the following acid products were produced: 3.7 g propionic acid and 0.7 g butyric acid. Esters were also present.

EXAMPLE 3

The procedure of Example 1 was exactly repeated except that the reactor was charged with a mixture of 0.50 g Ru$_3$(CO)$_{12}$, 0.20 g Mn$_2$(CO)$_{10}$, 2 ml of a solution of 57 percent HI, 25 ml acetic acid and 25 ml of acetic anhydride and the contents heated at 230° C. for two hours. Analysis by gas chromatography showed that the following acid products were produced: 8.0 g propionic acid and 2.6 g butyric acid. Esters were also present.

EXAMPLE 4

The procedure of Example 2 was exactly repeated except that the reactor was charged with 50 ml of propionic acid rather than acetic acid and the contents heated at 250° C. for two hours. Analysis by gas chromatography showed that the following acid products were produced: 3.2 g butyric acid and 0.32 g valeric acid. Esters were also observed.

EXAMPLE 5

The reactor of Example 1 was charged with a mixture of 0.50 g Ru$_3$(CO)$_{12}$, 1.0 g I$_2$, and 50 ml. of acetic acid. Equimolar amounts of CO and H$_2$ were then added to attain a pressure of 3000 psi at 25°. The contents were heated to 250° and shaken for two hours. Analysis by gas chromatography showed that 9.55 g of propionic acid and 1.59 g of butyric acid had been produced.

EXAMPLE 6

The procedure of Example 5 was followed exactly except that 0.60 g of I$_2$ was used instead of 1.0 g. Analysis by gas chromatography showed that 5.47 g of propionic acid and 1.00 g of butyric acid had been produced.

EXAMPLE 7

A 500 ml. stainless steel bomb reactor containing a removable glass liner was charged with a mixture of 1.0 gram of Ru$_3$(CO)$_{12}$, 2.0 ml. of a solution of 57 percent HI, and 50 ml. of acetic acid. Equimolar amounts of carbon monoxide and hydrogen were then added to the reactor to attain an initial pressure therein of 3000 psi at 25° C. The reactor was rocked and the contents heated at 260° C. and maintained at this temperature for two hours with continued rocking of the reactor. The reactor was then cooled and vented. The contents of the reactor were removed and analyzed by gas chromatography. This analysis showed the following products were produced: 8.51 grams of propionic acid, 1.26 grams of butyric acid, and much smaller amounts of esters.

EXAMPLE 8

The procedure of Example 7 was exactly repeated except that the reactor was charged with a mixture of 0.25 gram of Ru$_3$(CO)$_{12}$, 0.5 ml. of a solution of 57 percent HI, and 50 ml. of acetic acid. This analysis showed that the product mixture contained: 27.1 grams of acetic acid, 6.68 grams of propionic acid, 1.40 grams of butyric acid, and smaller amounts of esters.

What is claimed is:

1. The process for homologating a carbonyloxy-containing compound selected from the class of carboxylic acids, carboxylic acid esters and carboxylic acid anhydrides which comprises homologating the carbonyloxy-containing compound in the position alpha to the carbonyl of the carbonyloxy groups of the compound by reacting the carbonyloxy-containing compound with carbon monoxide and hydrogen in the presence of a ruthenium-containing compound, a manganese-containing compound, a proton donor, and iodine and/or an iodine compound at a temperature of between about 50° C. and about 400° C. and a pressure of between about 500 psia and about 12,500 psia.

2. The process of claim 1 wherein the ruthenium-containing compound is a ruthenium carbonyl complex.

3. The process of claim 1 wherein the proton donor is a hydrogen halide.

4. The process of claim 1 wherein the iodide promoter is a hydrogen iodide.

5. The process of claim 1 wherein the manganese-containing compound is provided in an amount such that the ratio of iodide atoms to manganese atoms is from about 2:1 to 50,000:1.

6. The process of claim 5 wherein the ratio is from 3:1 to 5,000:1.

7. The process of claim 6 wherein the ratio is from 5:1 to 2,500:1.

8. The process of claim 1 wherein the manganese-containing compound is a manganese halide.

9. The process of claim 1 wherein the manganese-containing compound is a manganese carbonyl.

10. The process of claim 1 wherein said carbonyloxy-containing compound is converted to a higher homolog differing by at least two —$CH_2$- units in the position alpha to the carbonyl of the carbonyloxy group.

* * * * *